(12) United States Patent
Steinle et al.

(10) Patent No.: US 9,563,186 B2
(45) Date of Patent: Feb. 7, 2017

(54) METHOD AND DEVICE FOR CONTROLLING APPARATUS

(71) Applicant: Brainlab AG, Feldkirchen (DE)

(72) Inventors: Wolfgang Steinle, Munich (DE); Nils Frielinghaus, Heimstetten (DE); Christoffer Hamilton, Gronsdorf (SE)

(73) Assignee: Brainlab AG, Feldkirchen (DE)

( * ) Notice: Subject to any disclaimer, the term of this patent is extended or adjusted under 35 U.S.C. 154(b) by 211 days.

(21) Appl. No.: 13/832,055

(22) Filed: Mar. 15, 2013

(65) Prior Publication Data

US 2013/0204428 A1 Aug. 8, 2013

Related U.S. Application Data

(63) Continuation of application No. PCT/EP2010/064456, filed on Sep. 29, 2010.

(51) Int. Cl.
*G06K 9/00* (2006.01)
*G05B 15/00* (2006.01)
(Continued)

(52) U.S. Cl.
CPC .............. *G05B 15/00* (2013.01); *G06F 3/011* (2013.01); *G06F 3/017* (2013.01); *G06F 19/3406* (2013.01)

(58) Field of Classification Search
CPC ............ G06K 9/00362; G06K 9/00369; G06K 9/00375; G06K 9/00382; G06K 9/00389; G06K 2009/00395; G06F 3/011; G06F 3/012; G06F 3/013; G06F 3/014; G06F 3/017; G06F 19/3406; G05B 15/00; G05B 15/02
See application file for complete search history.

(56) References Cited

U.S. PATENT DOCUMENTS 5,969,755 A 10/1999 Courtney
6,081,619 A 6/2000 Hashimoto et al.
(Continued)

FOREIGN PATENT DOCUMENTS

DE 10028435 C1 6/2000
EP 1 643 401 A1 4/2006
(Continued)

OTHER PUBLICATIONS

Wachs, "Gaze, Posture and Gesture Recognition to Minimize Focus Shifts for Intelligent Operating Rooms in a Collaborative Support System", Mar. 2010, CCC Publications, Int. Journal of Computers, Communications & Control, vol. 5, No. 1, p. 106-124.*
(Continued)

*Primary Examiner* — Stephen R Koziol
*Assistant Examiner* — Timothy Choi
(74) *Attorney, Agent, or Firm* — Tucker Ellis LLP

(57) ABSTRACT

A method for controlling a medical apparatus includes identifying at least one object and at least one part of a user's body; capturing the position, movement and/or alignment of the identified part of the body and the identified object; and controlling at least one apparatus using a corresponding predetermined command, if predetermined criteria for the identity of the object and/or part of the body and its position, movement and/or alignment are fulfilled. A device for controlling a medical apparatus includes an identifying device which identifies parts of a user's body and objects; a capture device which captures the position, movement and/or alignment of the identified parts of the body and objects; and a control device which controls at least one apparatus using a corresponding predetermined command, if predetermined criteria for the identity of the object and/or part of the body and its position, movement and/or alignment are fulfilled.

12 Claims, 1 Drawing Sheet

(51) Int. Cl.
*G06F 3/01* (2006.01)
*G06F 19/00* (2011.01)

(56) References Cited

U.S. PATENT DOCUMENTS

| | | |
|---|---|---|
| 6,359,612 B1 | 3/2002 | Peter et al. |
| 7,050,020 B2 | 5/2006 | Uehara et al. |
| 2007/0265527 A1* | 11/2007 | Wohlgemuth ......... A61B 6/547 600/424 |
| 2008/0097176 A1 | 4/2008 | Music et al. |
| 2008/0122786 A1* | 5/2008 | Pryor et al. .................. 345/156 |
| 2012/0071891 A1* | 3/2012 | Itkowitz ............. A61B 19/2203 606/130 |
| 2012/0229383 A1* | 9/2012 | Hamilton et al. ............ 345/158 |

FOREIGN PATENT DOCUMENTS

| | | | |
|---|---|---|---|
| WO | 2006/087689 A2 | 8/2006 | |
| WO | WO2012041371 * | 5/2012 | ............ G06F 19/00 |

OTHER PUBLICATIONS

International Search Report for International Application No. PCT/EP2010/064456 dated Mar. 29, 2011.

\* cited by examiner

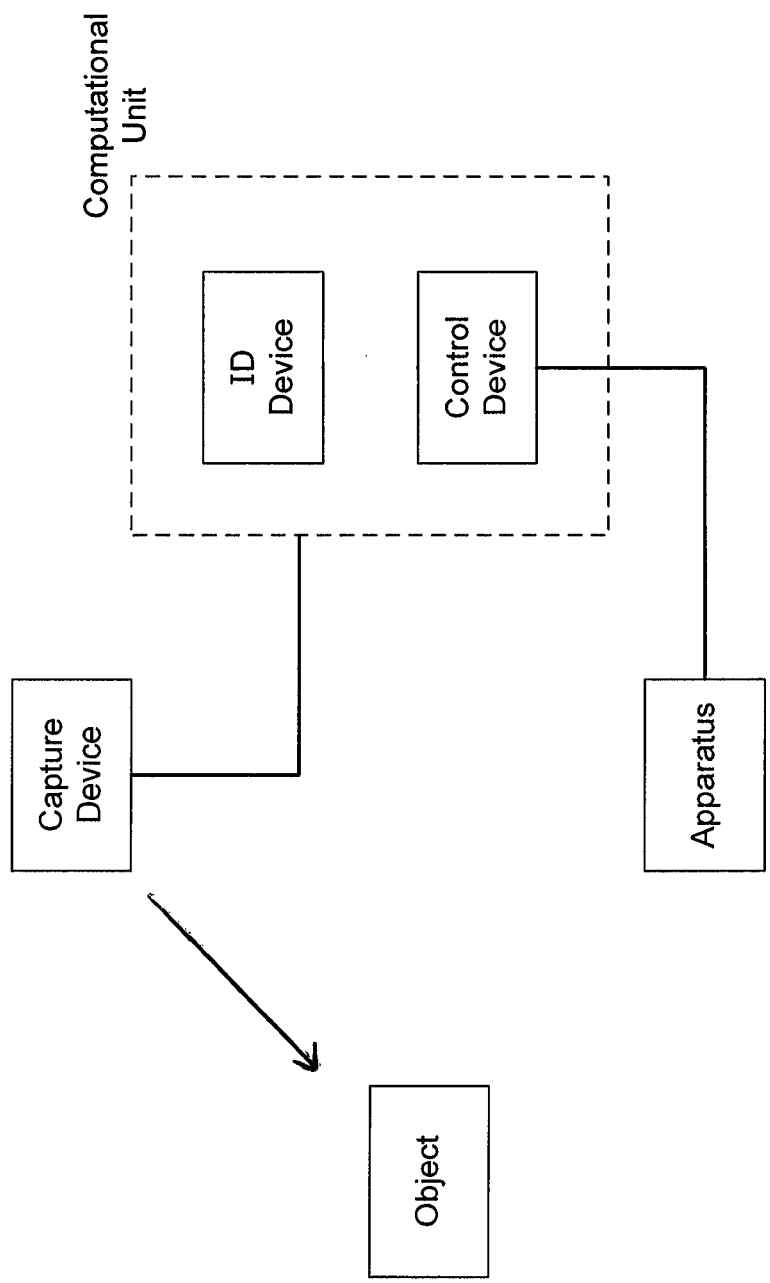

METHOD AND DEVICE FOR CONTROLLING APPARATUS

RELATED APPLICATION DATA

This application is a continuation of PCT/EP2010/064456, filed on Sep. 29, 2010, the contents of which is incorporated by reference herein in its entirety.

FIELD OF THE INVENTION

The invention relates to a method for controlling apparatus, in particular medical apparatus, which are only controlled when predetermined criteria with respect to identified objects and persons and/or parts of their bodies are fulfilled. The invention also relates to a device for performing such a method.

BACKGROUND OF THE INVENTION

In modern surgery, medical equipment is increasingly used to simplify the workflow and activities to be performed, not least in order to improve the success of a treatment. Operating such apparatus is however very complex, and inexperienced staff in particular are often out of their depth operating such apparatus. In the otherwise highly regimented workflow of operations which are to be performed, often under time pressure, this often leads to problems. These problems have hitherto been met by extensively training the medical staff in the equipment used and by using checklists, which however is very time-consuming.

SUMMARY OF THE INVENTION

A device and method in accordance with the present invention can reduce the required training to a necessary extent and to make it simpler, in particular for inexperienced staff, to operate a large variety of medical equipment. More particularly, an apparatus, such as a medical apparatus, can be controlled based on fulfilment of predetermined criteria for the identity of the object and/or part of the body and its/their position, movement and/or alignment.

BRIEF DESCRIPTION OF THE DRAWINGS

The forgoing and other embodiments of the invention are hereinafter discussed with reference to the drawings.

FIG. 1 is a block diagram illustrating components of an exemplary device in accordance with the present invention.

DETAILED DESCRIPTION

The method in accordance with the invention serves to control apparatus, in particular medical apparatus, and comprises the following steps:
- identifying at least one object and at least one part of a user's body;
- capturing the position, movement and/or alignment of the identified part of the body and the identified object;
- controlling at least one apparatus by means of a corresponding predetermined command, if predetermined criteria for the identity of the object and/or part of the body and its/their position, movement and/or alignment are fulfilled.

In other words, one or more objects as well as one or more parts of the body of one of the medical staff are identified in accordance with the method in accordance with the invention. Following this step, the objects and parts of the body of one of the medical staff participating in the method in accordance with the invention are already known. The term "object" as used here can encompass any medical equipment, including medical instruments within a treatment room such as for example infrared tracking camera arrays, microscopes, endoscopes, scalpels, bone machining tools or treatment tables. In addition, this is also intended to encompass objects and/or equipment not primarily used for medical purposes, such as for example 3D glasses, remote control devices, illumination systems, computational units and the like. "Parts of the body" can be understood here to mean in particular arms, hands, fingers, head, face, in particular ears and eyes, of the appointed medical staff.

In a second step of the method in accordance with the invention, the spatial position, movement and/or alignment of the identified objects and parts of the body is captured and also tracked. This step could also be referred to as spatially "tracking" the identified objects and parts of the body. In addition to the spatial identity of the objects and parts of the body, another set of parameters for the present method is known using this second step, namely the position, movement and/or alignment of the identified objects and parts of the body within the space being observed.

Markers could help to identify and/or track the objects and parts of the body. Based on the data obtained, a predetermined command can then be issued to an apparatus, depending on the values which the individual parameters have. In this way, one or more apparatus can be controlled using commands, such that they perform the issued command in accordance with a current situation and behave as desired.

In accordance with a preferred embodiment, the position, movement and/or alignment of the identified part of the body and the identified object relative to each other is thus captured, wherein the apparatus to be controlled is controlled by means of a corresponding and predetermined command, if a criterion for the relationship between the identified object and the identified part of the body is fulfilled.

Medical staff could for example "prompt" equipment to move using a hand movement. In very specific terms, medical staff could hold their hand over an operating table and cause the operating table to be raised or lowered by respectively moving their hand upwards or downwards. The criteria to be fulfilled would correspondingly be the position of the hand above the operating table and its movement upwards or downwards. A movement of the operating table could be correspondingly stopped by a sideways movement of the hand.

It would also be conceivable for equipment to be switched on as medical staff approach it and/or come within a predetermined distance of it, and similarly to be switched off again as soon as the medical staff depart from the equipment again and/or resume said distance.

In the aforementioned embodiment, it may be said that a command and/or control of an apparatus is dependent on a particular object-user relationship.

In accordance with another preferred embodiment of the present invention, the position, movement and/or alignment of an identified part of the body and an identified object relative to one or more other identified objects could additionally or alternatively form criteria which, when met, effect a command and/or control of an apparatus.

This may be described as an object-object-user relationship, which is a specification of an object-user relationship, wherein the number of objects is not limited. In accordance with the present invention, it is also conceivable for an apparatus which is to be controlled to simultaneously represent an identified object. A separation of an identified object and an apparatus to be controlled would obtain in the following example: as soon as medical staff pick up or touch equipment, corresponding operating instructions for the apparatus which has been touched are displayed on a screen.

An object-object-user relationship would for example obtain in the following:

In order to have operating instructions displayed to them on a screen, medical staff take the corresponding instrument or apparatus and hold it in front of the screen on which they would like the operating instructions to be displayed. The criteria in this case would be: holding the apparatus, which the medical staff are unclear about operating, in their hand; and moving the hand with the apparatus near to (and/or within a predetermined distance of) another apparatus (in this case, a screen).

In accordance with a preferred embodiment, "capturing" means optically capturing visual features of the object and/or part of the body, particularly preferably by means of at least one optical camera. In other words, one or more cameras are directed onto and monitor the region in which the objects and/or parts of the body to be captured are situated. This region can for example be a medical treatment room or part of a medical treatment room. The cameras can be connected to a computational unit which evaluates the camera images and identifies persons or parts of the body and objects in the images by means of image capture algorithms, wherein this also of course applies to moving images. It is also conceivable for parts of the bodies of a plurality of persons to be identified and captured.

The commands which are to be executed when predetermined criteria are met can be stored in a database, wherein it is also conceivable for this database to be able to be supplemented. If a new, hitherto unknown medical apparatus is to be used, it must first be "introduced" to the computational unit, which can for example be achieved by entering visual features of the apparatus into the database.

With reference to FIG. 1, another aspect of the present invention relates to a device for performing the method in accordance with the invention, wherein said device comprises: an identifying means which identifies parts of a user's body and objects; a capture means which captures the position, movement and/or alignment of the identified parts of the body and objects; and a control means which controls at least one apparatus by means of a corresponding predetermined command, if predetermined criteria for the identity of the object and/or part of the body and its position, movement and/or alignment are fulfilled.

In accordance with a preferred embodiment of the present invention which has already been described further above, said device can also—by means of the capture means—additionally capture the position, movement and/or alignment of the part of the body and the object relative to each other and/or relative to another object which is identified by the identifying means, wherein these data can form additional criteria which, when fulfilled or not fulfilled, effect a command and/or control of an apparatus.

The identifying means and the control means can then be encompassed by a computational unit and/or computer. Said computational unit can also be connected to the capture means which can comprise at least one optical camera for observing and capturing. As an alternative or in addition to one or more separate cameras for the capture means, it would also be conceivable for the capture means to avail itself of at least one optical camera which is assigned to a different apparatus. In other words, the capture means can access cameras which are part of equipment which is already provided anyway, such that it is at least partially possible to omit cameras which are provided especially for the capture means.

In the following, specific examples of using the present invention are given, wherein the invention can comprise features of the individual examples, individually or and in any expedient combination.

Controlling a tracking system: the capture means captures images from the operating theatre, wherein the medical staff and the camera array of the tracking system are identified and their position, movement and/or alignment is captured by means of an image capture algorithm. In this way, it is possible to ascertain whether the medical staff are attempting to align the camera array of the navigation system, for example when medical staff are captured in the vicinity of the camera array while the spatial alignment of the camera array is changing. Information on how the camera array is ideally to be positioned and/or aligned in order to obtain an optimum result can then be displayed to the medical staff by means of a screen.

Using 3D glasses: a screen can switch between 2D and 3D modes, as soon as an observing camera detects that at least one of the medical staff has put on 3D glasses (i.e. the position of the glasses and the position of the head and/or eyes of the person are close to each other). The switch between a 2D and 3D mode can also be made only once the person wearing 3D glasses stands in front of the corresponding screen and/or looks at the corresponding screen. The criteria which additionally have to be fulfilled in this case would thus be: the staff coming within a predetermined distance of the screen; and the head or the eyes being aligned towards the screen.

Controlling a medical microscope: a medical microscope is identified and its position captured by means of the at least one observing camera, wherein it is additionally possible to deduce from the distance between a person and the microscope and a change in the position, movement and/or alignment of the microscope whether the microscope is currently being used by a person. If this is the case, one or more screens in the treatment room can display the image obtained by the microscope. It would thus also be possible for one or more screens to only display the image obtained by the microscope once the microscope is placed over a patient. The image obtained could also be stored in a data memory in the form of a photograph or film, wherein it would also be conceivable for the "recording" to be stopped as soon as the microscope is no longer in use, which could be recognised by the fact that its spatial position is not changing and/or that no-one is standing in the vicinity of the microscope anymore. Other data provided by the microscope could also be recorded, for example zooming into and/or out of a region to be observed.

Using an endoscope: similar to the use of a microscope, the use of an endoscope by staff can also be detected by means of one or more observing cameras, wherein the room illumination could be reduced when the endoscope is being used.

Using a remote control device: the use of a remote control device, for example for a medical apparatus, by staff could also be detected by means of one or more observing cameras, wherein in this case, one or more screens could display information for using the corresponding remote control device.

Using a surgical instrument: equally, the use of a surgical instrument, for example a scalpel, by medical staff can be detected, wherein the sort and type of instrument could be identified by means of one or more observing cameras, and corresponding information for use could be outputted on a screen. It would thus for example be conceivable for the screen to switch to a "navigation mode" as soon as a pointer instrument is used or for medical staff to be made aware of the suitability or lack of suitability of a particular instrument for an activity to be performed when said instrument is used. When a particular instrument is used, it is also possible to record the period of time over which it is used.

Determining the level of activity: controlling an apparatus when predetermined criteria are fulfilled can also be understood to mean that the use of individual apparatus in the treatment room is registered and a computer is instructed to record a value for this "level of activity", such that it is possible to tell from without, for example when planning the occupation of rooms, whether people are working in the room in question. The intensity of the use of apparatus can also be captured, which can for example serve to estimate whether a treatment in the corresponding room will soon be finished, if only a few pieces of equipment or instruments are still being used.

Information on cable connections: in treatment rooms, there is a multitude of cable connections comprising corresponding plugs and sockets. As soon as a plug or socket of a cable connection is touched and/or held in the hand by medical staff, the corresponding plug connection—i.e. for example, the appropriate socket for the plug being held in the hand, or the appropriate plug for the touched socket on an apparatus, for example a screen—could be displayed by means of a screen. The corresponding plug and/or socket could also be spatially located by means of the observing camera, and its corresponding spatial position displayed to the medical staff on a screen. In this way, it is possible to simply locate the sockets or plugs sought. Such information could also be outputted only once the user holds a plug in front of the camera of the capture means, wherein the decisive criterion in this case is for example the position of the hand of the medical staff holding the plug, relative to the camera.

Identifying unknown apparatus: as soon as equipment, instruments or implants are to be used which are unknown to the navigation system being used, they could be held in front of a camera of the capture means which identifies the manufacturer and type, for example on the basis of a serial number or bar code, such that the navigation system can retrieve the necessary data for the as yet unknown equipment, instrument or implant from a database.

Screenshot: if an apparatus which is being held in the hand comprises a camera which is directed onto a screen in the treatment room (criteria: position of the apparatus in the hand; position of the hand/apparatus near the screen; apparatus and/or camera aligned onto the screen), it would be conceivable for a "screenshot" or recording of the screen image which the instrument camera is currently directed onto to be produced by instructing a corresponding computational unit.

Phone book: as soon as medical staff reach for a telephone or hold one in their hand, operating instructions or a phone book directory for the corresponding telephone could be displayed on one or more screens in the treatment room. It would be equally conceivable for such a display to only be shown when the telephone is held in front of a camera for the capture means.

Drugs and expendable material: drug containers and packaging and expendable materials could be held in front of a camera of the capture means as soon as they are empty, such that a corresponding order for the drug or expendable material which has been used up is placed by a computational unit.

What is claimed is:

1. A method for controlling at least one of a plurality of medical apparatus, comprising:
    identifying at least two of the plurality of medical apparatus and at least one body part of a user controlling the at least one of the plurality of medical apparatus, the at least two medical apparatus and the at least one body part of the user being within a field of view of at least one optical camera, the field of view including an operating theatre;
    capturing a position, movement and/or alignment of the at least one identified body part of the user and the at least two identified medical apparatus relative to each other; and
    controlling at least one of the plurality of medical apparatus via a corresponding predetermined command, said controlling being effected through a fulfilment of predetermined criteria for the identity and the respective position, movement and/or alignment relative to each other of the at least two medical apparatus and the at least one body part of the user.

2. The method according to claim 1, wherein capturing includes optically capturing visual features of the object and/or at least one body part.

3. The method according to claim 2, wherein optically capturing includes using at least one optical camera to capture the visual features.

4. The method according to claim 1, wherein identifying and/or capturing is/are performed within a predetermined space.

5. The method according to claim 4, wherein the predetermined space is a medical treatment room.

6. The method according to claim 1, wherein body parts of a plurality of users are captured and identified.

7. The method according to claim 1, wherein the predetermined command is stored in a database.

8. The method according to claim 1, further comprising capturing the controls exercised within a predetermined space in order to determine the level of activity within the space.

9. A device for controlling at least one of a plurality of medical apparatus, comprising:
    an identification device configured to identify at least one body part of a user controlling at least one of the plurality of medical apparatus, and at least two of the plurality of medical apparatus, the at least two medical apparatus and the at least one part of the user's body being within a field of view of at least one optical camera, the field of view including an operating theatre;
    a capture device configured to capture a position, movement and/or alignment of the at least one identified part of the user's body and the at least two identified medical apparatus relative to each other; and
    a control device configured to control at least one of the plurality of medical apparatus via a corresponding predetermined command, said control device configured to control the at least one medical apparatus effected through a fulfilment of predetermined criteria for the identity and the position, movement and/or alignment relative to each other of the at least two medical apparatus and the at least one body part of the user.

10. The device according to claim 9, wherein a computational unit comprises the identification device and the control device.

11. The device according to claim 9, wherein the capture device comprises at least one optical camera.

12. The device according to claim 9, wherein the capture device avails itself of at least one optical camera which is assigned to an apparatus.

* * * * *